(12) United States Patent
Ting

(10) Patent No.: US 9,486,180 B2
(45) Date of Patent: Nov. 8, 2016

(54) CHESTPIECE OF A STETHOSCOPE

(71) Applicant: MDF Instruments USA, Inc., Westlake Village, CA (US)

(72) Inventor: Darren Talun Chiao Ting, Malibu, CA (US)

(73) Assignee: MDF Instruments USA, Inc., Westlake Village, CA (US)

( * ) Notice: Subject to any disclaimer, the term of this patent is extended or adjusted under 35 U.S.C. 154(b) by 0 days.

(21) Appl. No.: 14/605,706

(22) Filed: Jan. 26, 2015

(65) Prior Publication Data

US 2015/0129350 A1 May 14, 2015

Related U.S. Application Data

(63) Continuation-in-part of application No. 13/929,420, filed on Jun. 27, 2013, now Pat. No. 8,939,251.

(60) Provisional application No. 61/665,257, filed on Jun. 27, 2012.

(51) Int. Cl.
*A61B 7/02* (2006.01)
*A61B 7/04* (2006.01)
*A61B 7/00* (2006.01)

(52) U.S. Cl.
CPC .................................. *A61B 7/02* (2013.01)

(58) Field of Classification Search
CPC .......... A61B 7/02; A61B 7/00; A61B 7/026; A61B 7/04
USPC .............................. 181/131; 381/67; 600/528
See application file for complete search history.

(56) References Cited

U.S. PATENT DOCUMENTS 2,233,087 A * 2/1941 Tynan ...................... A61B 7/02
181/131
2,513,827 A * 7/1950 Tynan .................... A61B 7/026
137/625.32

(Continued)

FOREIGN PATENT DOCUMENTS

CN 202235434 U 5/2012
CN 103536311 A 1/2014

OTHER PUBLICATIONS

MDF Instruments Stethoscope Collection Brochure, dated May 10, 2011.

(Continued)

*Primary Examiner* — Edgardo San Martin
(74) *Attorney, Agent, or Firm* — The Law Office of Patrick F. O'Reilly III, LLC

(57) ABSTRACT

A chestpiece of a stethoscope is disclosed herein. The stethoscope chestpiece includes a chestpiece body portion with an elongate recess disposed therein; a rotatable acoustic valve assembly rotatably disposed in the elongate recess of the chestpiece body portion, the rotatable acoustic valve assembly being selectively positionable between a first operative position and a second operative position and configured to regulate the transmission of sound waves through the chestpiece of the stethoscope, the rotatable acoustic valve assembly including a rotatable body portion with a circumferential groove formed therein; and a pin positioned within the chestpiece body portion, the pin configured to prevent an axial movement of the rotatable acoustic valve assembly within the chestpiece body portion by engaging with the circumferential groove of the rotatable body portion. In one or more embodiments, the stethoscope chestpiece includes a substantially transparent non-chill ring disposed on a diaphragm or bell thereof.

17 Claims, 9 Drawing Sheets

(56) References Cited

U.S. PATENT DOCUMENTS

| | | | | |
|---|---|---|---|---|
| 2,722,989 A * | 11/1955 | Tynan | A61B 7/026 181/131 |
| 3,035,656 A * | 5/1962 | Kebel | A61B 7/026 181/137 |
| 3,152,659 A * | 10/1964 | Littmann | A61B 7/026 181/137 |
| 3,224,526 A * | 12/1965 | Weber | A61B 7/026 181/137 |
| 3,303,903 A * | 2/1967 | Speelman | A61B 7/026 181/131 |
| 3,316,998 A * | 5/1967 | Krug | A61B 7/026 181/137 |
| 3,366,198 A * | 1/1968 | Littmann | A61B 7/02 181/137 |
| 4,239,089 A | 12/1980 | Nelson | |
| 4,475,619 A * | 10/1984 | Packard | A61B 7/026 181/137 |
| 4,569,413 A * | 2/1986 | Allen | A61B 7/026 181/131 |
| 4,669,572 A | 6/1987 | Fassbender | |
| 4,770,270 A * | 9/1988 | Grimm | A61B 7/026 181/131 |
| 4,802,550 A | 2/1989 | Poore | |
| 4,940,023 A * | 7/1990 | Shue | A61B 7/026 600/528 |
| 5,022,487 A | 6/1991 | Kirchner | |
| 5,252,787 A | 10/1993 | Moore et al. | |
| 5,389,747 A | 2/1995 | Mohrin | |
| 5,498,841 A * | 3/1996 | Allen | A61B 7/02 181/131 |
| 5,774,563 A * | 6/1998 | DesLauriers | A61B 7/04 381/67 |
| 5,910,992 A * | 6/1999 | Ho | A61B 7/026 181/131 |
| 5,945,641 A * | 8/1999 | Shieh | A61B 7/02 181/131 |
| 5,952,618 A * | 9/1999 | Deslauriers | A61B 7/026 181/131 |
| 6,202,784 B1 | 3/2001 | Alatriste | |
| 6,308,798 B1 * | 10/2001 | Rashman | A61B 7/026 181/131 |
| 6,454,045 B1 | 9/2002 | Ryan | |
| 6,932,186 B2 | 8/2005 | Costa et al. | |
| 7,036,627 B2 | 5/2006 | Costa et al. | |
| 7,441,629 B2 * | 10/2008 | Krysztof | A61B 7/02 181/131 |
| 8,939,251 B2 * | 1/2015 | Ting | A61B 7/02 181/131 |
| 2002/0186850 A1 * | 12/2002 | Deslauriers | A61B 7/04 381/67 |
| 2008/0245602 A1 | 10/2008 | Nakamura | |
| 2010/0155173 A1 | 6/2010 | Boyd et al. | |
| 2014/0005574 A1 | 1/2014 | Ting | |

OTHER PUBLICATIONS

MDF Instruments Product Brochure, dated earlier than Apr. 2012 (exact date unknown).
MDF Instruments ProCardial Stethoscope Brochure, dated Apr. 4, 2012.
MDF Instruments Cardio-X Stethoscope Brochure, dated Mar. 15, 2012.
First office action on the merits (Non-Final Rejection) in U.S. Appl. No. 13/929,420, mailed on Jun. 5, 2014.
Notice of Allowance in U.S. Appl. No. 13/929,420, mailed on Sep. 19, 2014.

* cited by examiner

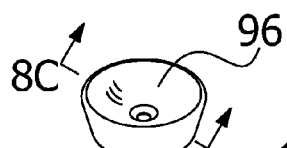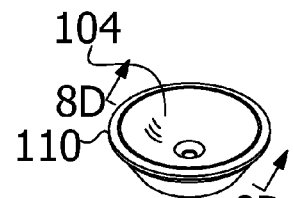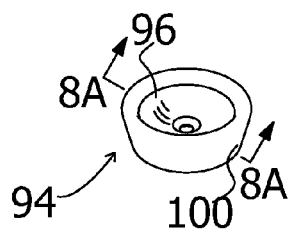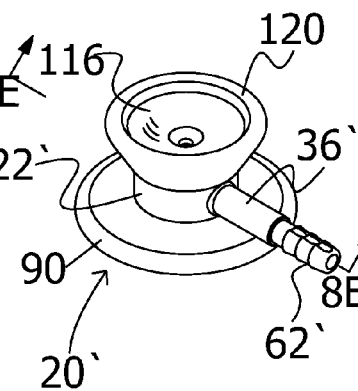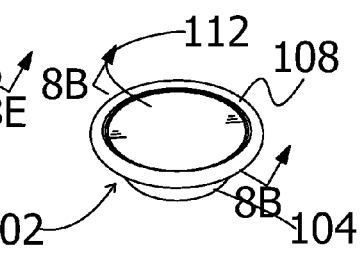
FIG. 6A  FIG. 6B  FIG. 6C  FIG. 6D  FIG. 6E
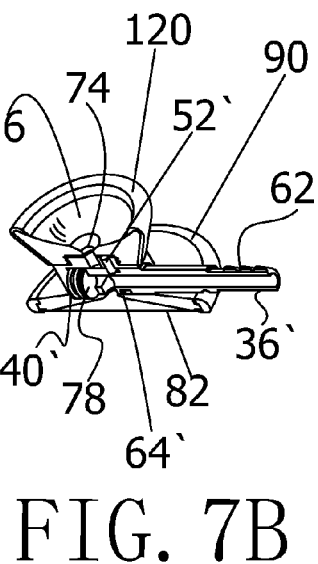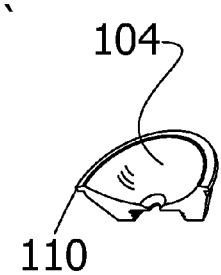
FIG. 7A  FIG. 7B  FIG. 7C

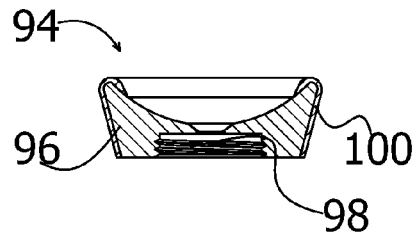
FIG. 8A
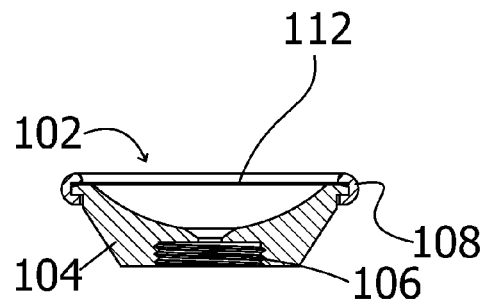
FIG. 8B
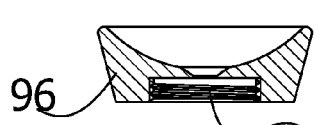
FIG. 8C
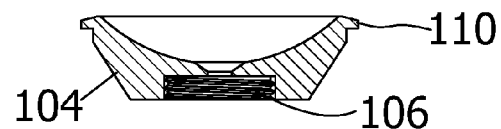
FIG. 8D
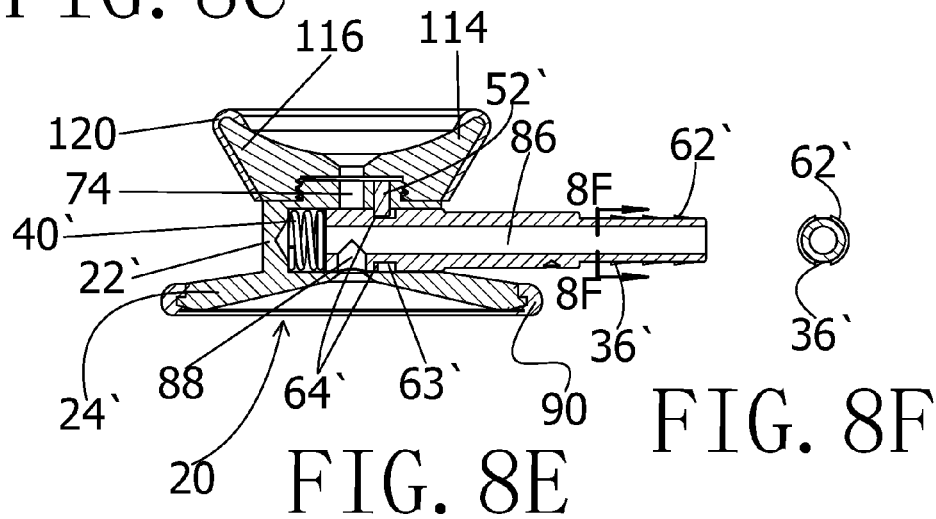
FIG. 8E
FIG. 8F

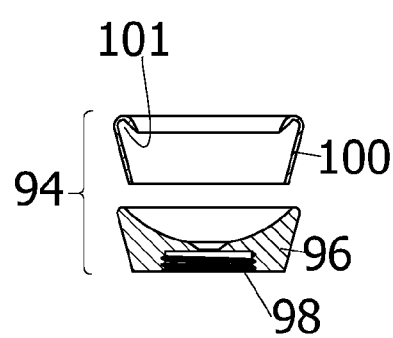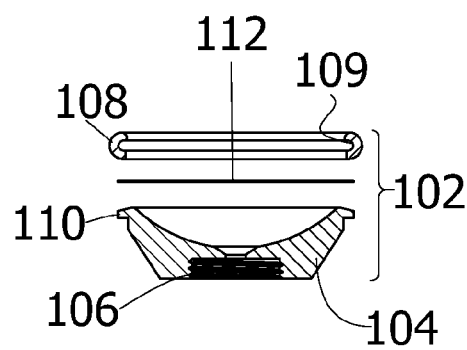
FIG. 10A  FIG. 10B
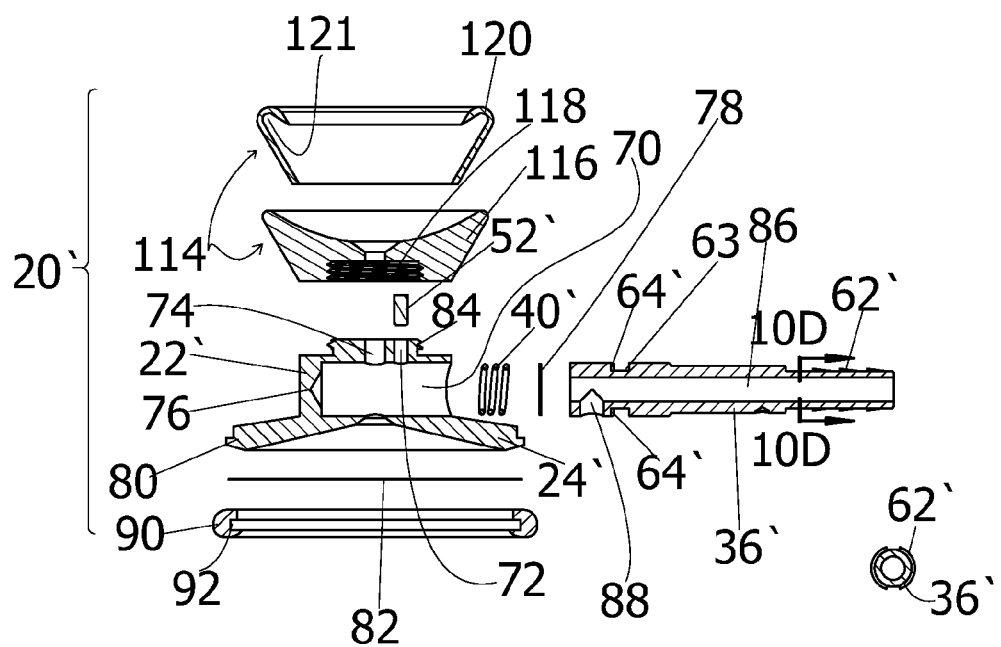
FIG. 10C  FIG. 10D

CHESTPIECE OF A STETHOSCOPE

CROSS-REFERENCE TO RELATED APPLICATIONS

This is a continuation-in-part of U.S. patent application Ser. No. 13/929,420, entitled "Stethoscope with Light Source and/or Timepiece", filed on Jun. 27, 2013, and further claims the benefit of U.S. Provisional Patent Application No. 61/665,257, entitled "Stethoscope With Light Source And Timepiece", filed on Jun. 27, 2012, the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to stethoscopes and more particularly to a stethoscope having a light suitable for patient examination and a readily accessible time source when needed to improve monitoring patients during general examination, and a chestpiece of a stethoscope with a rotatable valve assembly and/or transparent non-chill rings.

2. Background and Description of Related Art

It is known in the art that a medical practitioner employs various devices during the course of examination of a patient. One such instrument is a stethoscope that is used by physicians, nurses, and paramedics in the early stage of any general examination and/or proper vital sign examination of a patient.

A stethoscope is an acoustic medical device for auscultation, or listening to the internal sounds of a body. It is often used to listen to heart sounds. It is also used to listen to intestines and blood flow in arteries and veins. Acoustic stethoscopes operate on the transmission of sounds from the chestpiece, via air-filled hollow tubes, to a binaural (headset) that a practitioner uses to listen to the acoustic sounds of a patient. The chestpiece usually consists of a diaphragm and a housing that supports the diaphragm within the chestpiece body. When the diaphragm is placed on the patient, body sounds vibrate the diaphragm, creating acoustic pressure waves which travel up the tubing to the binaural and the listener's ears.

The proper operation of a stethoscope is essential, since a practitioner, nurse or a doctor, uses a stethoscope to listen to the sounds of a patient's body to determine normal functioning and abnormalities.

In addition to stethoscopes, medical practitioners may use flash lights to examine the eyes of a patient for pupil dilation and reaction and/or use a time measurement device that would allow them to monitor a patient's heart or breathing rate. These additional instruments may be stored at various examination stations and may not be accessible in a timely manner by practitioners when needed. As such, a crucial part of the vital sign exams may be missed simply because clinicians do not have the proper tools in their possession. For example, clinicians may not conduct a pupillary response evaluation because they do not have a light handy, or may miss monitoring the heart rate because they do not have a time measuring device in their possession. In addition, medical practitioners often need to listen to multiple types of heart sounds having different frequency characteristics, or may need to treat different types of patients, such as adults, children, and infants. Also, conventional stethoscopes that are utilized by medical practitioners are readily susceptible to cross-contamination due to particulate buildup thereon, particularly on the components of the stethoscope that come into contact with patients, such as the stethoscope chestpiece components.

Therefore, what is needed is a multi-functional instrument including a plurality of devices that could be utilized by a medical practitioner to conduct a proper vital sign examination of a patient in a timely manner. Moreover, an instrument is needed that enables clinicians to easily conduct the crucial vital sign examination as a part of all general examinations. Furthermore, what is needed is an instrument that permits a clinician to check a plurality of the patient's vital signs without necessitating the removal of multiple instruments. In addition, what is needed is a stethoscope with a versatile chestpiece comprising sound regulation means and/or multiple attachments for enabling the stethoscope to be easily used for listening to heart sounds having varying frequency characteristics, and for use in treating different types of patients, such as adults, children, and infants. Also, there is a need for a stethoscope chestpiece comprising components that readily enable a user of the stethoscope to identify the buildup of particulate matter thereon.

BRIEF SUMMARY OF EMBODIMENTS OF THE INVENTION

Accordingly, the present invention is directed to a chestpiece of a stethoscope that substantially obviates one or more problems in the related art hereinbefore discussed.

In accordance with one aspect of one or more embodiments of the present invention, there is provided a chestpiece of a stethoscope, which includes a chestpiece body portion having a first end and a second end, the chestpiece body portion including an elongate recess disposed therein; a rotatable acoustic valve assembly rotatably disposed in the elongate recess of the chestpiece body portion, the rotatable acoustic valve assembly being selectively positionable between a first operative position and a second operative position, the rotatable acoustic valve assembly including a rotatable body portion with a circumferential groove formed therein, the rotatable acoustic valve assembly being configured to regulate the transmission of sound waves through the chestpiece of the stethoscope; and a pin positioned within the chestpiece body portion, the pin configured to prevent an axial movement of the rotatable acoustic valve assembly within the chestpiece body portion by engaging with the circumferential groove of the rotatable body portion of the rotatable acoustic valve assembly.

In a further embodiment of this aspect of the present invention, the stethoscope chestpiece further comprises a spring disposed within the chestpiece body portion, the spring configured to further prevent the axial movement of the rotatable acoustic valve assembly inside the chestpiece body portion.

In yet a further embodiment, the rotatable body portion of the rotatable acoustic valve assembly comprises a first end portion and a second end portion disposed opposite to the first end portion, the first end portion of the rotatable acoustic valve assembly disposed within the chestpiece body portion, the second end portion of the rotatable body portion having a plurality of barbs for engaging an acoustic tube of a binaural assembly.

In still a further embodiment, the pin comprises a linear body with a first end and a second end, the linear body of the pin extending from the first end proximate to the first end of the chestpiece body portion to the second end disposed in the circumferential groove of the rotatable body portion of the rotatable acoustic valve assembly, the pin being stationarily disposed within an aperture of the chestpiece body portion, and the rotatable body portion of the rotatable acoustic valve assembly being configured to rotate relative to the pin.

In yet a further embodiment, the stethoscope chestpiece further comprises two notches disposed in a circular sidewall bounding the circumferential groove of the rotatable body portion of the rotatable acoustic valve assembly, the two notches being spaced approximately 180 degrees apart from one another, and each of the two notches configured to receive the pin therein.

In still a further embodiment, a first of the two notches defines the first operative position of the rotatable acoustic valve assembly, and a second of the two notches defines the second operative position of the rotatable acoustic valve assembly, the two notches configured to provide a user with tactile feedback as to a proper positioning of the rotatable acoustic valve assembly in either the first operative position or the second operative position.

In yet a further embodiment, the stethoscope chestpiece further comprises a spring disposed within the chestpiece body portion, the spring configured to further prevent the axial movement of the rotatable acoustic valve assembly inside the chestpiece body portion, and the spring configured to apply an axial force against the rotatable body portion of the rotatable acoustic valve assembly so that the pin snaps into place in one of the two notches.

In still a further embodiment, the rotatable body portion of the rotatable acoustic valve assembly further includes a longitudinal acoustic passageway portion extending a length thereof and a transverse acoustic passageway portion extending generally perpendicular to the longitudinal acoustic passageway portion, the longitudinal acoustic passageway portion being fluidly coupled to the transverse acoustic passageway portion.

In yet a further embodiment, the circumferential groove of the rotatable body portion of the rotatable acoustic valve assembly is disposed between the transverse acoustic passageway portion of the rotatable body portion and a barbed end portion of the rotatable body portion.

In accordance with another aspect of one or more embodiments of the present invention, there is provided a chestpiece of a stethoscope, which includes a chestpiece body portion having a first end and a second end, the chestpiece body portion including an elongate recess disposed therein; a diaphragm attached to the first end of the chestpiece body portion; a rotatable acoustic valve assembly rotatably disposed in the elongate recess of the chestpiece body portion, the rotatable acoustic valve assembly being selectively positionable between a first operative position and a second operative position, the rotatable acoustic valve assembly including a rotatable body portion with a circumferential groove formed therein, the rotatable acoustic valve assembly being configured to regulate the transmission of sound waves through the chestpiece of the stethoscope; and a pin positioned within the chestpiece body portion, the pin configured to prevent an axial movement of the rotatable acoustic valve assembly within the chestpiece body portion by engaging with the circumferential groove of the rotatable body portion of the rotatable acoustic valve assembly.

In a further embodiment of this aspect of the present invention, the rotatable body portion of the rotatable acoustic valve assembly comprises a first end portion and a second end portion disposed opposite to the first end portion, the first end portion of the rotatable acoustic valve assembly disposed within the chestpiece body portion, the second end portion of the rotatable body portion having a plurality of barbs for engaging an acoustic tube of a binaural assembly.

In yet a further embodiment, the pin comprises a linear body with a first end and a second end, the linear body of the pin extending from the first end proximate to the first end of the chestpiece body portion to the second end disposed in the circumferential groove of the rotatable body portion of the rotatable acoustic valve assembly, the pin being stationarily disposed within an aperture of the chestpiece body portion, and the rotatable body portion of the rotatable acoustic valve assembly being configured to rotate relative to the pin.

In still a further embodiment, the stethoscope chestpiece further comprises two notches disposed in a circular sidewall bounding the circumferential groove of the rotatable body portion of the rotatable acoustic valve assembly, the two notches being spaced approximately 180 degrees apart from one another, and each of the two notches configured to receive the pin therein.

In yet a further embodiment, a first of the two notches defines the first operative position of the rotatable acoustic valve assembly, and a second of the two notches defines the second operative position of the rotatable acoustic valve assembly, the two notches configured to provide a user with tactile feedback as to a proper positioning of the rotatable acoustic valve assembly in either the first operative position or the second operative position.

In still a further embodiment, the stethoscope chestpiece further comprises a spring disposed within the chestpiece body portion, the spring configured to further prevent the axial movement of the rotatable acoustic valve assembly inside the chestpiece body portion, and the spring configured to apply an axial force against the rotatable body portion of the rotatable acoustic valve assembly so that the pin snaps into place in one of the two notches.

In yet a further embodiment, the rotatable body portion of the rotatable acoustic valve assembly further includes a longitudinal acoustic passageway portion extending a length thereof and a transverse acoustic passageway portion extending generally perpendicular to the longitudinal acoustic passageway portion, the longitudinal acoustic passageway portion being fluidly coupled to the transverse acoustic passageway portion.

In still a further embodiment, the circumferential groove of the rotatable body portion of the rotatable acoustic valve assembly is disposed between the transverse acoustic passageway portion of the rotatable body portion and a barbed end portion of the rotatable body portion.

In accordance with yet another aspect of one or more embodiments of the present invention, there is provided a chestpiece of a stethoscope, which includes a chestpiece body portion having a first end and a second end, the second end being oppositely disposed with respect to the first end;

a diaphragm or a bell attached to at least one of the first and second ends of the chestpiece body portion; and a non-chill ring disposed about a circumference of the diaphragm or the bell, the non-chill ring being formed from a substantially transparent material so that accumulated particulate matter on the non-chill ring is readily visible to a user of the stethoscope.

In a further embodiment of this aspect of the present invention, the diaphragm or the bell comprises an annular projection extending outwardly from a peripheral side thereof, and wherein the non-chill ring comprises a circumferential internal groove disposed therein, the annular projection of the diaphragm or the bell configured to matingly engage with the circumferential internal groove of the non-chill ring.

In yet a further embodiment, the chestpiece body portion comprises both the diaphragm attached to the first end thereof and the bell attached to the second end thereof, the diaphragm being fixedly attached to the first end of the chestpiece body portion, and the bell being removably attached to the second end of the chestpiece body portion so that a plurality of different attachments are capable of being selectively attached to the second end of the chestpiece body portion by a user of the stethoscope.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 6A is a top perspective view of a body portion of a first type of stethoscope chestpiece attachment, according to an embodiment of the invention;

FIG. 6B is a top perspective view of a body portion of a second type of stethoscope chestpiece attachment, according to an embodiment of the invention;

FIG. 6C is a top perspective view of the first type of stethoscope chestpiece attachment in an assembled state, the body portion of the first type of stethoscope chestpiece attachment being depicted in FIG. 6A;

FIG. 6D is an assembled perspective view of a stethoscope chestpiece assembly of a stethoscope, according to another embodiment of the invention;

FIG. 6E is a top perspective view of the second type of stethoscope chestpiece attachment in an assembled state, the body portion of the second type of stethoscope chestpiece attachment being depicted in FIG. 6B;

FIG. 7A is a cutaway perspective view of the body portion of the first type of stethoscope chestpiece attachment illustrated in FIG. 6A;

FIG. 7B is a cutaway perspective view of the stethoscope chestpiece assembly illustrated in FIG. 6D;

FIG. 7C is a cutaway perspective view of the body portion of the second type of stethoscope chestpiece attachment illustrated in FIG. 6B;

FIG. 8A is a cross-sectional view of the first type of stethoscope chestpiece attachment, which is cut along the cutting-plane line 8A-8A in FIG. 6C;

FIG. 8B is a cross-sectional view of the second type of stethoscope chestpiece attachment, which is cut along the cutting-plane line 8B-8B in FIG. 6E;

FIG. 8C is a cross-sectional view of the body portion of the first type of stethoscope chestpiece attachment, which is cut along the cutting-plane line 8C-8C in FIG. 6A;

FIG. 8D is a cross-sectional view of the body portion of the second type of stethoscope chestpiece attachment, which is cut along the cutting-plane line 8D-8D in FIG. 6B;

FIG. 8E is a cross-sectional view of the stethoscope chestpiece assembly, which is cut along the cutting-plane line 8E-8E in FIG. 6D;

FIG. 8F is a cross-sectional view of the rotatable valve body portion, which is cut along the cutting-plane line 8F-8F in FIG. 8E;

FIG. 10A is an exploded cross-sectional view of the first type of stethoscope chestpiece attachment illustrated in FIGS. 6C and 8A;

FIG. 10B is an exploded cross-sectional view of the second type of stethoscope chestpiece attachment illustrated in FIGS. 6E and 8B;

FIG. 10C is an exploded cross-sectional view of the stethoscope chestpiece assembly illustrated in FIGS. 6D and 8E; and FIG. 10D is a cross-sectional view of the rotatable valve body portion, which is cut along the cutting-plane line 10D-10D in FIG. 10C.

Throughout the figures, the same parts are always denoted using the same reference characters so that, as a general rule, they will only be described once.

DETAILED DESCRIPTION OF THE PREFERRED EMBODIMENT(S) OF THE INVENTION

The exemplary embodiment of the stethoscope assembly described below includes several integrated assemblies and subassemblies. One assembly is a chestpiece assembly with a chestpiece body and a diaphragm component securely attached to the chestpiece body. The chestpiece assembly also comprises a switch subassembly that is operatively connected to a light source subassembly for turning the light emitting element on and off. The switch subassembly further includes a rotatable acoustic valve that is operatively connected to a positive adherent point (i.e., a conductive element with a contact point or points) and allows a clinician to prevent the transmission of an acoustic wave from the diaphragm through the binaural assembly when the light source is on. The light source subassembly is secured to chestpiece body of the stethoscope and provides a practitioner with a practical medical device for a vital sign examination. The chestpiece assembly of the stethoscope also includes a timepiece subassembly which is secured to chestpiece body of the stethoscope and is configured to measure time during a vital sign examination. The light emitting element and the timepiece are powered by a battery. The stethoscope also includes a binaural assembly comprising an acoustic tube connected to an acoustic valve subassembly that allows patients' body sounds to travel from the diaphragm component to a practitioner's ear. The acoustic valve is a part of the switch subassembly and regulates auscultating as described hereinbelow.

Figure 1:
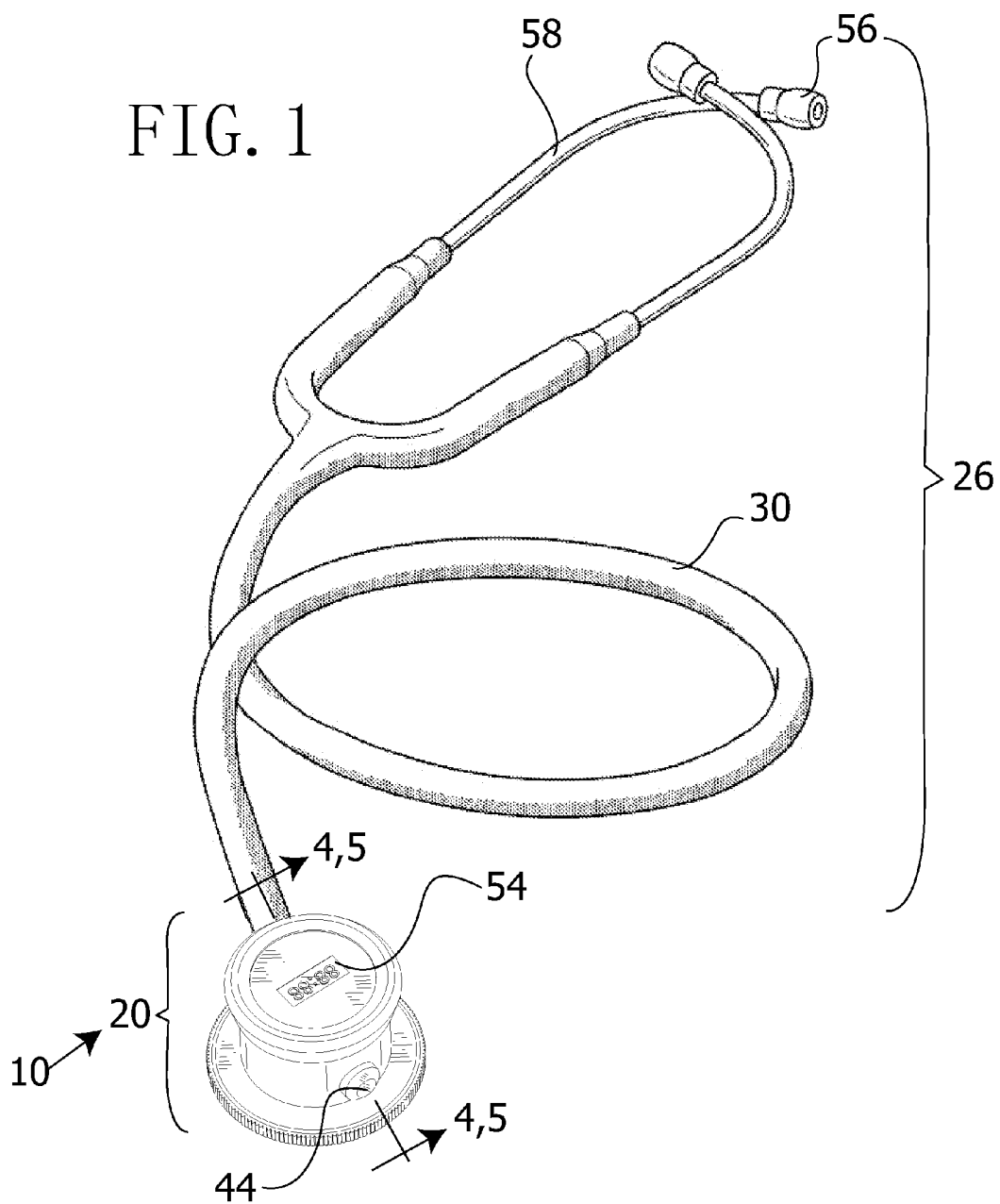
FIG. 1 is a perspective view of a stethoscope with a light source and a timepiece, according to one embodiment of the invention.

Referring now to the drawings and the reference characters marked thereon, and specifically to FIG. 1, stethoscope 10 made in accordance with one embodiment of the invention includes a chestpiece assembly 20 and a binaural assembly 26 that includes at least one earpiece 56. In the herein described embodiment of FIG. 1, the binaural assembly 26 includes two earpieces 56 wherein the depicted stethoscope 10 is a binaural stethoscope. As shown in FIG. 1, the binaural assembly 26 of the stethoscope 10 includes an acoustic tube 30 that is acoustically coupled to a headset with two (2) ear tubes 58. Each of the ear tubes 58 is provided with a respective earpiece 56 disposed on the end thereof.

Figure 3:
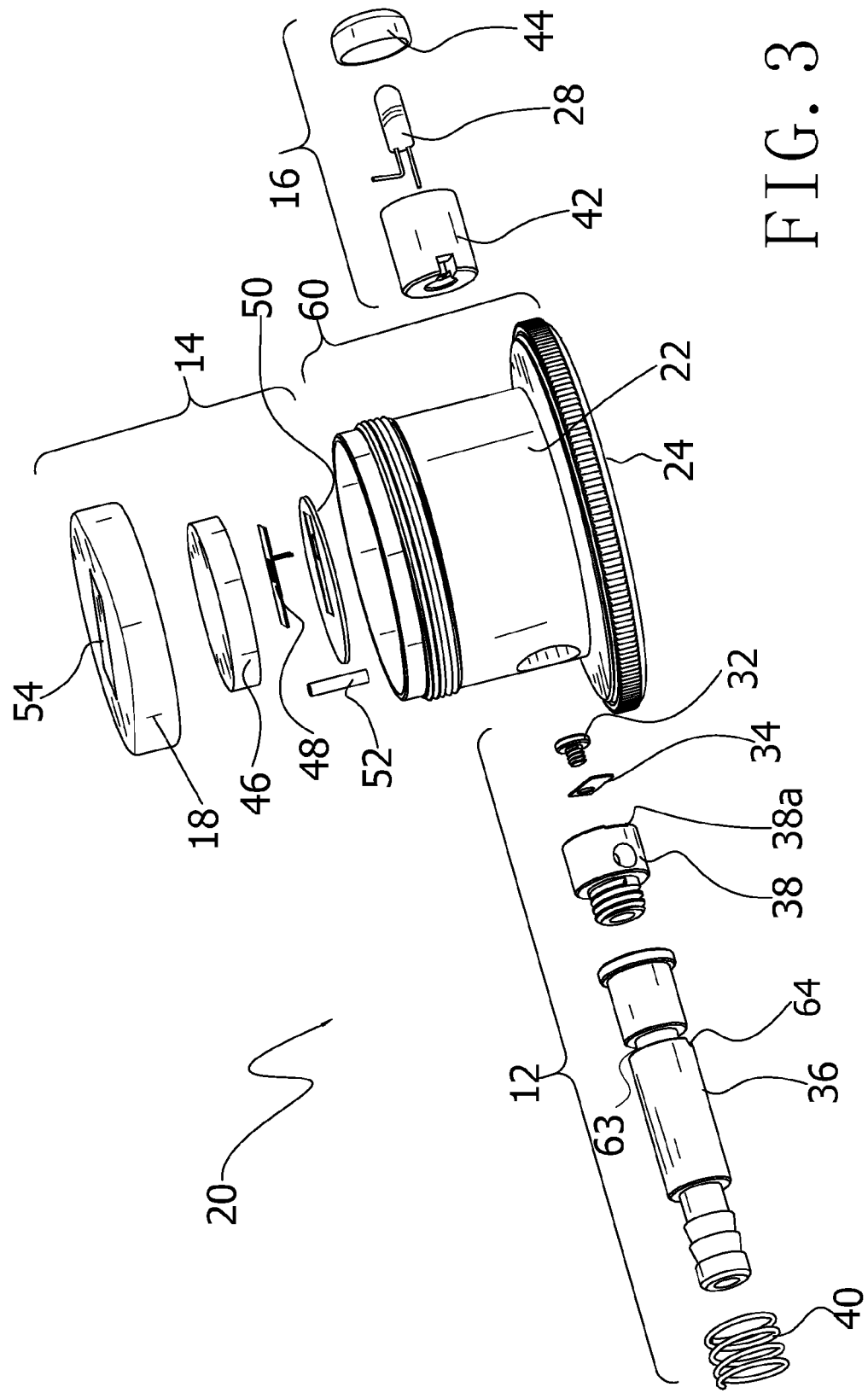
FIG. 3 is an exploded perspective view of the chestpiece assembly of the stethoscope, according to the embodiment of FIG. 1.

FIG. 3 depicts an exploded view of the chestpiece assembly 20 of the stethoscope for proper physical examination of a patient, the stethoscope being designated generally as 10. The chestpiece assembly 20 includes a switch subassembly 12, a power source subassembly 14, a light source subassembly 16, a time piece subassembly 18, and a chestpiece body subassembly 60.

The chestpiece body subassembly 60 includes a chestpiece body 22 and a diaphragm component 24 which is securely attached to a first end of the chestpiece body 22 to intercept and amplify acoustic sounds of a patient during physical examination. The chestpiece body 22 is configured to transmit the acoustic sounds to the binaural assembly 26 shown in FIG. 1. The binaural assembly 26 includes an acoustic tube 30 which is connected to switch subassembly 12 with the rotatable acoustic valve 38.

The switch subassembly 12 that also operates as the valve of the sound is operably connected to the light source subassembly 16 to turn the light emitting element 28 on and off. The light source subassembly 16 is operatively connected to the chestpiece body 22 for allowing a practitioner to examine vital signs of a patient. The light source subassembly 16 includes a light emitting element 28.

In an exemplary embodiment, the light emitting element 28 is in the form of an incandescent, filament-type light bulb with an input voltage of approximately 3.0 volts (approximately 3.0 V) and an amperage of approximately 0.20 milliamps (approximately 0.20 mA). In an alternative embodiment, the light emitting element 28 is in the form of a light emitting diode (LED) light source. However, depending on its rated light output (e.g., in lumens), it is noted that an LED light source might be too bright for a patient's eye when a pupil reflex exam is being conducted using the stethoscope 10.

The timepiece subassembly 18 is securely connected to the second end of the chestpiece body 22 and is configured to measure time during a vital sign examination of a patient. The power source subassembly 14 is operatively connected to the timepiece subassembly 18 and to the light source subassembly 16 (i.e., it is electrically coupled to each of these subassemblies 16, 18), and thus, provides power to each of these two subassemblies 16, 18.

Figure 4:
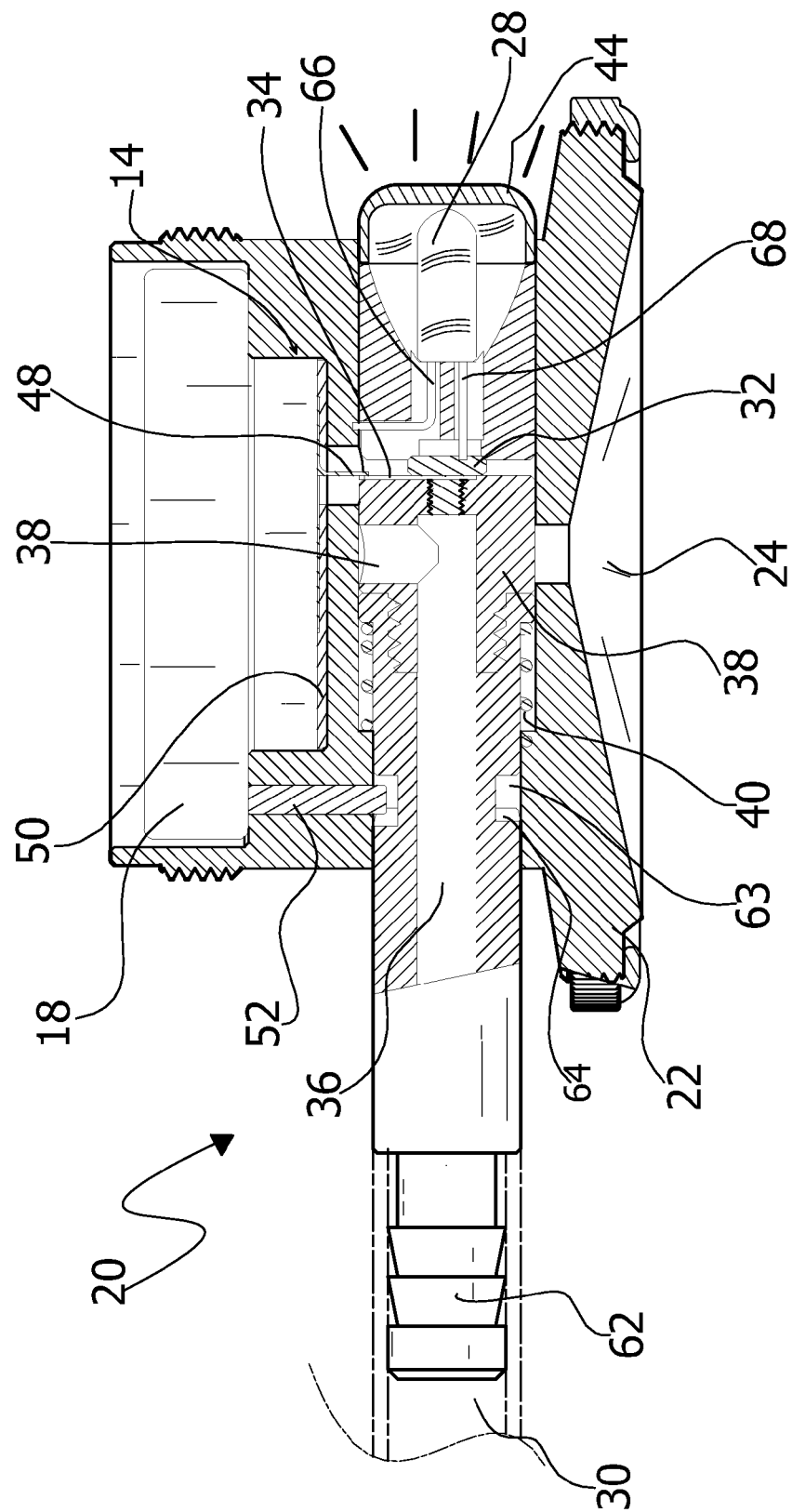
FIG. 4 is a cross-sectional view of the chestpiece assembly of the stethoscope cut along the cutting-plane line 4-4 in FIG. 1, wherein the light source is illustrated in an "on" position and the acoustic valve is in a closed position so as to prevent the transmission of sounds through the acoustic tube.
Figure 5:
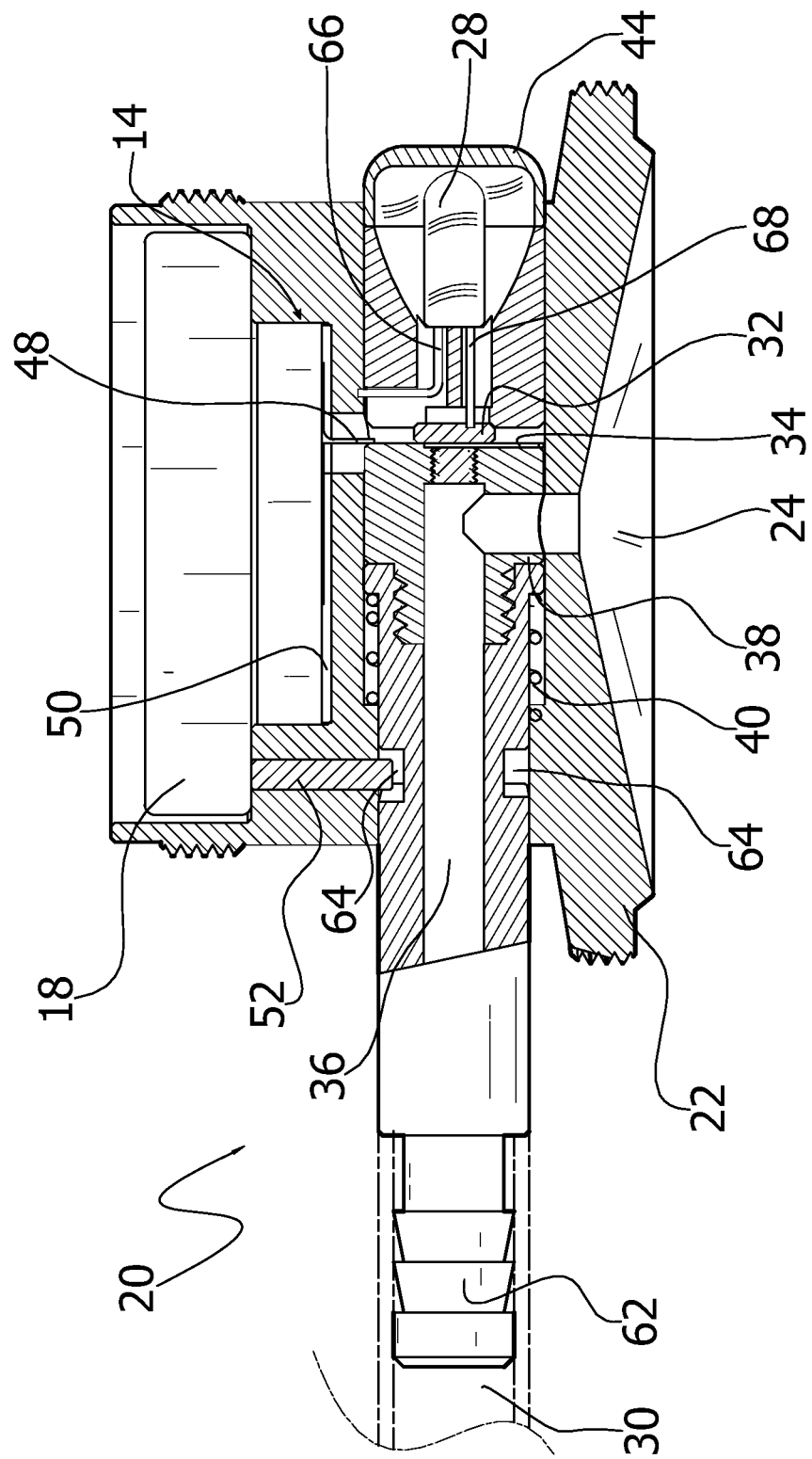
FIG. 5 is a cross-sectional view of the chestpiece assembly of the stethoscope cut along the cutting-plane line 5-5 in FIG. 1, wherein the light source is illustrated in an "off" position and the acoustic valve is in a open position so as to permit the transmission of sounds through the acoustic tube.

The switch subassembly 12 may include a positive adherent point element 32 (in the form of a conductive screw element, e.g., a metallic screw) that is operatively connected to a positive connecting sheet 34 (i.e., a generally planar conductive element 34 with an aperture disposed therein for receiving conductive screw element 32). As shown in FIG. 3, the end of the rotatable acoustic valve 38 is provided with a notch 38a disposed therein for receiving the positive connecting sheet 34 (conductive element 34). The positive connecting sheet 34 (conductive element 34) is configured to engage and disengage a positive adherent sheet 48 (i.e., a conductive element 48) of power source subassembly 14 as the rotating tubular shaft 36 of the switch subassembly 12 turns. The engagement and disengagement of the positive connecting sheet 34 (conductive element 34) of switch subassembly 12 and positive adherent sheet 48 (conductive element 48) of the power source subassembly 14 will selectively control an electrical current pathway for powering the light emitting element 28 on and off. When the positive connecting sheet 34 (conductive element 34) is engaged with the positive adherent sheet 48 (conductive element 48), an electrical current pathway is formed between the power source subassembly 14 and the light emitting element 28. In particular, as illustrated in FIGS. 4 and 5, the electrical lead 68 of the light emitting element 28 engages the conductive screw element 32 which, in turn, engages the conductive element 34 that engages conductive element 48. As also shown in FIGS. 4 and 5, the other electrical lead 66 of the light emitting element 28 engages an internal wall of the chestpiece body 22. Conversely, when the positive connecting sheet 34 (conductive element 34) is disengaged from the positive adherent sheet 48 (conductive element 48), the electrical current pathway between the power source subassembly 14 and the light emitting element 28 is interrupted (i.e., open circuit state) so as to prevent electrical current flow.

The switch subassembly 12 also includes a rotatable acoustic valve 38 which is configured to be operatively connected to the positive adherent point 32 (conductive screw element) for preventing an acoustic wave from traveling through the binaural assembly 26 when the light source is on.

The rotatable tubular shaft 36 of switch subassembly 12 is operatively connected to rotatable acoustic valve 38 at a first end and the binaural assembly 26 on a second end. In particular, as shown in FIG. 3, the rotatable acoustic valve 38 is provided with a plurality of external threads for matingly engaging with a plurality of internal threads in the first end of the rotatable tubular shaft 36. In addition, as shown in FIGS. 4 and 5, the second end of the rotatable tubular shaft 36 is provided with a barbed end 62 for securely engaging the end of the acoustic tube 30. The switch subassembly 12 may also include a spring 40 disposed within the chestpiece body 22 to prevent axial movement of the rotatable tubular shaft 36 inside the chestpiece body 22, and to facilitate engagement of the pin 52 with the notches 64 (i.e., the spring 40 applies an axial force to the rotatable tubular shaft 36 so that the pin 52 "clicks" into the notches 64). As such, by maintaining the pin 52 within one of the notches 64, the spring 40 prevents the rotatable tubular shaft 36 from inadvertently rotating out of one of its two operational positions, which are described hereinafter.

The light source subassembly 16 is configured to be connected to the chestpiece body 22. The light source subassembly 16 includes a socket 42 which is disposed within a cavity of the chestpiece body 22, where the socket has a mouth allowing the light emitting element 28 to be disposed in the socket 42 for emitting light in response to being energized by battery 46 of power source subassembly 14. The light source subassembly 16 also includes a transparent dome-like cover 44 which is disposed over the mouth of the socket 42.

The timepiece subassembly 18 includes a timepiece 54 which is mounted on the chestpiece body 22 and is powered by the battery 46 of power source subassembly 14. In an alternative embodiment, the timepiece subassembly 18 includes its own separate battery for powering the timepiece 54 within the housing of the timepiece subassembly 18. The timepiece subassembly may include a timepiece 54 that is a digital or analog clock.

Figure 2:
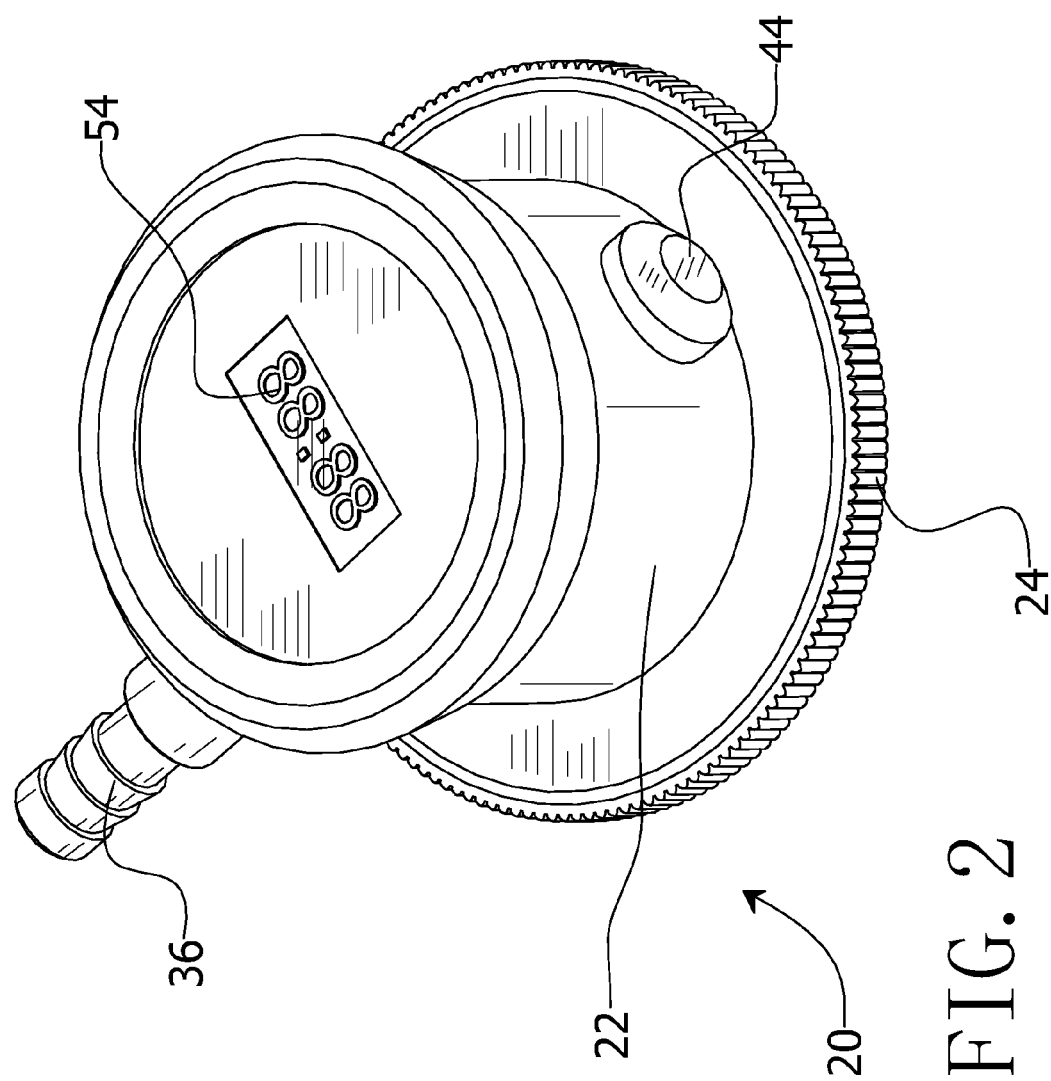
FIG. 2 is an assembled perspective view of the chestpiece assembly of the stethoscope, according to the embodiment of FIG. 1.

As shown in FIGS. 1 and 2, in the illustrated embodiment, the timepiece 54 is provided with a digital display (e.g., a liquid crystal display (LCD) display). In an exemplary embodiment, the timepiece 54 has an input voltage of approximately 1.5 volts (approximately 1.5 V) and an amperage of approximately 0.07 milliamps (approximately 0.07 mA). However, it is to be understood that the timepiece 54 could be embodied in other suitable forms (e.g., an analog-type clock), and could have other suitable input voltages and amperages. While the timepiece 54 could be embodied as an analog movement-type clock, it is noted that such a movement-type clock could potentially cause noise in the chestpiece assembly 20, and thus, interfere with heart sounds.

The power source subassembly 14 includes a battery 46 for providing power to timepiece 54 of timepiece subassembly 18 and/or the light source subassembly 16 through the positive adherent sheet 48. An electrical current pathway is established from the battery 46 to the light emitting element 28 when positive adherent sheet 48 is operatively engaged with the positive connecting sheet 34. The power source subassembly 14 may also include an insulating sheet 50, for preventing contact between the positive adherent sheet 48 and the chestpiece body 22. In an exemplary embodiment, the battery 46 is in the form of a lithium button cell battery with an output voltage of approximately 3.0 volts (approximately 3.0 V) and an output amperage of approximately 0.20 milliamps (approximately 0.20 mA). However, it is to be understood that the battery 46 can be embodied in other suitable forms as well, with other suitable output voltages and currents.

The power source subassembly 14 also includes a rod or pin 52 positioned within the chestpiece body 22 which mainly restricts the axial movement of the rotatable tubular shaft 36 within the chestpiece body 22. As best shown in FIGS. 3-5, the circumferential groove 63 disposed about the periphery of the rotatable tubular shaft 36 (i.e., the acoustic valve stem) accommodates the pin 52, which holds the rotatable tubular shaft 36 in place. That is, the pin 52 is inserted through chestpiece body 22 into the circumferential groove 63 of the rotatable tubular shaft 36 so as to hold the rotatable tubular shaft 36 inside the chestpiece body 22. In addition, as depicted in FIGS. 3-5, there are two (2) small notches 64 in the groove 63 that are spaced approximately 180 degrees apart. Each of these two (2) notches 64 is configured to receive the pin 52 therein. These notches 64 give the user of the stethoscope 10 important tactile feedback for the proper first operational position (i.e., light "on" and acoustic valve "closed" position—FIG. 4) and the proper second operational position (i.e., light "off" and acoustic valve "open" position—FIG. 5 position). Without the tactile feedback afforded by the engagement between the pin 52 and each respective notch 64, it would be difficult for the user of the stethoscope 10 to find the proper rotational positions of the rotatable tubular shaft 36, which comprise each of these abovedescribed two operational states. As a result, without this tactile feedback, the user would most likely rotate the rotatable tubular shaft 36 to partially open and partially closed intermediate positions, which could compromise both the functionality of the light source subassembly 16 and the acoustical performance of the stethoscope 10.

Referring now to FIG. 4, the light emitting source 28 is shown in an "on" operating position. In this cross-sectional view of the chestpiece assembly 20 of the stethoscope 10, the positive adherent point element 32 of switch subassembly 12 is configured to operatively connect the positive connecting sheet 34 with the positive adherent sheet 48 of power source subassembly 14, to develop a current pathway resulting in turning the light emitting source 28 on. The engagement and disengagement of positive connecting sheet 34 of switch subassembly 12 with the positive adherent sheet 48 of power source subassembly 14 is controlled by the position of rotatable tubular shaft 36. Furthermore, rotatable acoustic valve 38 is configured with respect to the rotation of rotatable tubular shaft 36 to prevent body sounds of patients transmitted through the acoustic tube 30 when the light emitting source 28 is on.

FIG. 5 illustrates an exemplary embodiment of the chestpiece assembly 20 of the stethoscope 10 wherein the light emitting source 28 is in an "off" position. In this cross-sectional view of chestpiece body 22, the positive adherent point element 32 (conductive screw element) still contacts the electrical lead 68 of the light emitting element 28, but the positive connecting sheet 34 (conductive element), which is operatively connected to the positive adherent point element 32, is disengaged from the positive adherent sheet 48 (conductive element) of power source subassembly 14, thereby opening the electrical circuit and preventing electrical current flow to the light emitting element 28. This configuration is made possible by rotation of rotatable tubular shaft 36 of switch subassembly 12, furthermore positioning the rotatable acoustic valve 38 to be fluidly coupled with diaphragm component 24 allowing the patient's body sound to be intercepted, amplified and transmitted through the acoustic tube 30 and be heard by the practitioner. When the rotatable tubular shaft 36 of switch subassembly 12 is rotated 180 degrees by the user of the stethoscope 10 (i.e., by the user grasping the portion of the rotatable tubular shaft 36 that is disposed externally from the chestpiece body 22 and twisting it—see FIGS. 2, 4, and 5), the positive connecting sheet 34 (conductive element) is simultaneously rotated along with the rotatable tubular shaft 36 from the position of FIG. 5 to the position of FIG. 4. In the FIG. 4 position, as described above, the positive connecting sheet 34 (conductive element) engages the positive adherent sheet 48 (conductive element) so as to form an electrical current pathway between the power source subassembly 14 and the light emitting element 28, thereby turning the light "on".

It is readily apparent that the aforedescribed inventive stethoscope 10 offers numerous advantages. First, the stethoscope 10 includes a plurality of devices that could be utilized by a medical practitioner to conduct a proper vital sign examination of a patient in a timely manner. In particular, when used in conjunction with a sphygmomanometer, the stethoscope 10 allows clinicians to properly check four (4) out the five (5) primary vital signs. The stethoscope 10 of the aforedescribed embodiment combines many of the major tools (i.e., a stethoscope, light and timepiece) required for a vital sign examination, thereby enabling clinicians to properly conduct their vital sign examinations. By virtue of its timepiece, the inventive stethoscope 10 allows measurement of respiratory rate and heart rate by a clinician. Moreover, the stethoscope 10 permits a clinician to check a plurality of the patient's vital signs without necessitating the removal of the instrument. Specifically, the novel switch subassembly 12 of the stethoscope 10 allows auscultating while the physician is able to keep the ear-tips inside his or her ear. Furthermore, the stethoscope 10 allows a clinician to turn off the sound and use the light for a pupil exam without removing the headset. The switch subassembly 12 of the stethoscope 10 provides a safety mechanism for clinicians by prohibiting the transmission of a loud sound if the chestpiece accidently knocks against a non-human object. Advantageously, the features of the inventive stethoscope 10 give the clinician the flexibility to use all three tools at once without having to remove the headset if, for example, the clinician wants to auscultate once again.

Now, with reference to FIGS. 6A-10D, another embodiment of a stethoscope chestpiece assembly 20' will be described in detail. Initially, as shown in FIGS. 6D, 8E, and 10C, it can be seen that the stethoscope chestpiece 20' generally includes a chestpiece body portion 22' having a first end and a second end, the chestpiece body portion 22' including an elongate recess 70 disposed therein; a diaphragm 24' attached to the first end of the chestpiece body portion 22'; a removable bell attachment 114 attached to the second end of the chestpiece body portion 22'; a rotatable acoustic valve assembly 36', 78 rotatably disposed in the elongate recess 70 of the chestpiece body portion 22', the rotatable acoustic valve assembly 36', 78 being selectively positionable between a first operative position (e.g., in which sounds are transmitted from the diaphragm 24' to the user of the stethoscope) and a second operative position (e.g., in which sounds are transmitted from the removable bell attachment 114 to the user of the stethoscope), the rotatable acoustic valve assembly 36', 78 including a rotatable body portion 36' with a circumferential groove 63' disposed therein, the rotatable acoustic valve assembly 36', 78 being configured to regulate the transmission of sound waves through the chestpiece 20' of the stethoscope; and a pin 52' positioned within the chestpiece body portion 22', the pin 52' configured to prevent an axial movement of the rotatable acoustic valve assembly 36', 78 within the chestpiece body portion 22' by engaging with the circumferential groove 63' of the rotatable body portion 36' of the rotatable acoustic valve assembly 36', 78.

As best illustrated in FIGS. 8E and 10C, the rotatable body portion 36' of the rotatable acoustic valve assembly 36', 78 includes a longitudinal acoustic passageway portion 86 extending a length thereof and a transverse acoustic passageway portion 88 extending generally perpendicular to the longitudinal acoustic passageway portion 86. In these figures, it can be seen that the longitudinal acoustic passageway portion 86 is fluidly coupled to the transverse acoustic passageway portion 88 so that sounds received from the selected one of the diaphragm 24' and the bell 114 of the stethoscope chestpiece 20' can be transmitted through the rotatable acoustic valve assembly 36', 78 to the binaural assembly of the stethoscope. The longitudinal acoustic passageway portion 86 of the rotatable body portion 36' comprises two oppositely disposed open ends at the respective longitudinal ends thereof. The first open end of the longitudinal acoustic passageway portion 86 is closed by a circular cover plate 78 so that sounds waves are not transmitted into the interior of the chestpiece body portion 22', while the second open end of the longitudinal acoustic passageway portion 86 is configured to be coupled with the acoustic tubing of the binaural assembly of the stethoscope. As best depicted in FIG. 8E, the circumferential groove 63' of the rotatable body portion 36' of the rotatable acoustic valve assembly 36', 78 is disposed between the transverse acoustic passageway portion 88 of the rotatable body portion 36' and the second open end of the longitudinal acoustic passageway portion 86 of the rotatable body portion 36'.

Referring collectively to FIGS. 6D, 7B, 8E, and 10C, it can be seen that the rotatable body portion 36' of the rotatable acoustic valve assembly 36', 78 comprises a first end portion and a second end portion disposed opposite to the first end portion. The first end portion of the rotatable acoustic valve assembly 36', 78 is disposed within the chestpiece body portion 22' in the assembled state of the chestpiece 20', while the second end portion of the rotatable body portion 36' has a barbed end portion 62' with a plurality of barbs for engaging an acoustic tube of a binaural assembly (e.g., by elastically deforming the flexible acoustic tube).

Figures 9A, 9B:
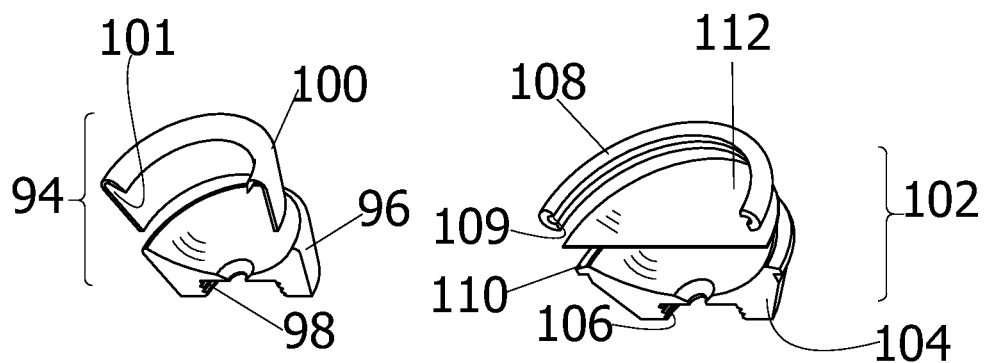
FIG. 9A is an exploded cutaway perspective view of the first type of stethoscope chestpiece attachment illustrated in FIG. 6C.
FIG. 9B is an exploded cutaway perspective view of the second type of stethoscope chestpiece attachment illustrated in FIG. 6E.
Figure 9C:
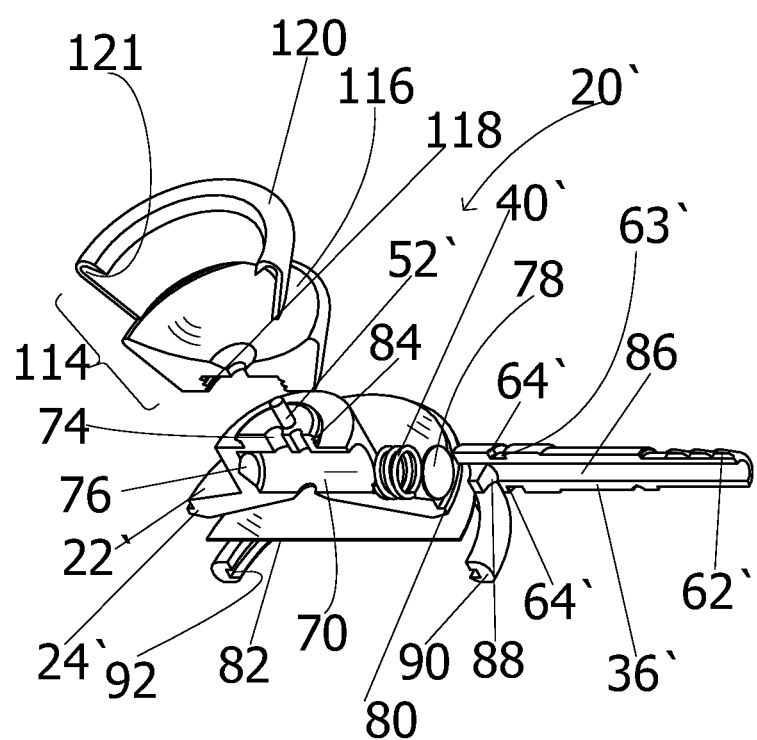
FIG. 9C is an exploded cutaway perspective view of the stethoscope chestpiece assembly illustrated in FIG. 6D.

As described above, the rotatable body portion 36' of the rotatable acoustic valve assembly 36', 78 is received within an elongate recess 70 of the chestpiece body portion 22'. Referring particularly to FIGS. 9C and 10C, it can be seen that the elongate recess 70 of the chestpiece body portion 22' has a generally cylindrical shape for accommodating the generally cylindrical shape of the rotatable body portion 36'. Also, the closed end of the cylindrically shaped elongate recess 70 comprises a conical bore 76 formed in the chestpiece body portion 22' (see FIGS. 9C and 10C). The conical bore 76 at the end of the elongate recess 70 is created during the machining of the recess 70 (e.g., by a drill bit with a conical tip).

Turning to FIGS. 7B, 8E, 9C, and 10C, the pin 52' of the stethoscope chestpiece 20' will be described in further detail. As shown in these figures, the pin 52' comprises a linear cylindrical body with a first end and a second end. In the assembled state of the stethoscope chestpiece 20', the linear cylindrical body of the pin 52' extends from its first end, which is proximate to the first end of the chestpiece body portion 22' with bell attachment 114, to its second end, which is disposed in the circumferential groove 63' of the rotatable body portion 36' of the rotatable acoustic valve assembly 36', 78. The pin 52' of the stethoscope chestpiece 20' engages with the circumferential groove 63' of the rotatable body portion 36', and selectively engages the notches 64' of the rotatable body portion 36', which will be described hereinafter. The pin 52' is stationarily disposed within a pin aperture 72 of the chestpiece body portion 22' (see FIG. 10C) such that the rotatable body portion 36' of the rotatable acoustic valve assembly 36', 78 is configured to rotate relative to the pin 52'.

Referring again to FIGS. 7B, 8E, 9C, and 10C, it can be seen that the rotatable body portion 36' of the rotatable acoustic valve assembly 36', 78 further comprises two notches 64' disposed in one of the two circular sidewalls bounding the circumferential groove 63' of the rotatable body portion 36' (e.g., the circular sidewall closest to the first end portion of the rotatable body portion 36'). As shown in the illustrated embodiment, the two notches 64' are spaced approximately 180 degrees apart from one another, and each of the two notches 64' is configured to receive the pin 52' therein. A first of the two notches 64' defines the first operative position of the rotatable acoustic valve assembly 36', 78 (e.g., in which sounds are transmitted from the diaphragm 24' to the user of the stethoscope), and a second of the two notches 64' defines the second operative position of the rotatable acoustic valve assembly 36', 78 (e.g., in which sounds are transmitted from the removable bell attachment 114 to the user of the stethoscope). As will be described hereinafter, the two notches 64' are configured to provide a user with tactile feedback as to a proper positioning of the rotatable acoustic valve assembly 36', 78 in either the first operative position or the second operative position.

Similar to that described above for the embodiment of FIGS. 1-5, each of the notches 64' gives the user of the stethoscope important tactile feedback for the proper first operative position (i.e., when the acoustic passageway portions 86, 88 of the rotatable body portion 36' are fluidly coupled with the diaphragm 24'—FIG. 8E position) and the proper second operative position (i.e., when the acoustic passageway portions 86, 88 of the rotatable body portion 36' are fluidly coupled with the removable bell attachment 114 via the upper acoustic passageway 74 in the chestpiece body portion 22'). Without the tactile feedback afforded by the engagement between the pin 52' and each respective notch 64', it would be difficult for the user of the stethoscope to find the proper rotational positions of the rotatable body portion 36', which comprise each of these abovedescribed two operational states. As a result, without this tactile feedback, the user would most likely rotate the rotatable body portion 36' to partially open and partially closed intermediate positions, which could compromise the functionality of the acoustical performance of the stethoscope.

Next, with reference to FIGS. 7B, 8E, 9C, and 10C, the spring 40' of the stethoscope chestpiece 20' will now be described. As shown in FIG. 8E, the helical spring 40' is disposed within the chestpiece body portion 22' in the assembled state of the stethoscope chestpiece 20'. The spring 40' is configured to prevent the inadvertent axial movement of the rotatable acoustic valve assembly 36', 78 inside the chestpiece body portion 22' by applying axial force thereagainst. As such, inadvertent sliding of the rotatable body portion 36' is thereby prevented. The axial force applied by the spring 40' enables the pin 52' to snap into place in one of the two notches 64'. That is, as described above with regard to the embodiment of FIGS. 1-5, the spring 40' facilitates engagement of the pin 52' with the notches 64' (i.e., the spring 40' applies an axial force to the rotatable tubular shaft 36' so that the pin 52' "clicks" into the notches 64'). As such, by maintaining the pin 52' within one of the notches 64', the spring 40' prevents the rotatable tubular shaft 36' from inadvertently rotating out of one of its two operative positions, which were described above.

As described above, the stethoscope chestpiece 20' has a diaphragm 24' attached to the first, lower end thereof, and a removable bell attachment 114 attached to the second, upper end thereof (see FIGS. 6D, 7B, and 8E). The diaphragm 24' is fixedly secured to the lower end of the stethoscope chestpiece 20' in a non-removable manner, while the bell attachment 114 is attached to the second, upper end of the stethoscope chestpiece 20' in a detachable manner. Turning to the exploded sectional view of FIG. 10C, it can be seen that the diaphragm 24' includes an annular projection 80 for accommodating a transparent non-chill ring 90 and a disklike diaphragm membrane 82. The transparent non-chill ring 90 of the lower diaphragm 24' comprises a circumferential internal groove 92 that receives the annular projection 80 of the lower diaphragm 24'. In the illustrated embodiment, the transparent non-chill ring 90 is formed from a resilient material that elastically deforms when the circumferential internal groove 92 of the transparent non-chill ring 90 is matingly engaged with the annular projection 80 of the diaphragm 24'. As also shown in FIGS. 9C and 10C, the removable bell attachment 114 comprises an inverted frustoconical body portion 116 with a plurality of internal threads 118 disposed in a bottom cylindrical recess thereof. The plurality of internal threads 118 in the bottom cylindrical recess of the frustoconical body portion 116 threadingly engage with a plurality of external threads 84 disposed on a cylindrical projection or boss extending from the top of the chestpiece body portion 22'. As such, a user is able to easily remove the bell attachment 114 from the chestpiece body portion 22' when it is desired to utilize another type of attachment on the top of the stethoscope chestpiece 20'. Referring to FIGS. 8E and 10C, similar to the transparent non-chill ring 90 of the lower diaphragm 24', it can be seen that an upper transparent non-chill ring or cover 120 with upper peripheral recess 121 fits over the inverted frustoconical body portion 116 of the bell 114. That is, the upper transparent non-chill ring or cover 120 is formed from a resilient material that elastically deforms when the upper peripheral recess 121 of the upper transparent non-chill ring or cover 120 is matingly engaged with the top peripheral rim of the inverted frustoconical body portion 116 of the bell attachment 114. The details of the transparent non-chill rings 90, 100, 108, 120 will be described hereinafter.

Advantageously, various top attachment pieces can be interchangeably used with stethoscope chestpiece 20' so that the stethoscope comprising the stethoscope chestpiece 20' may be used for various patient applications (e.g., measuring different sounds associated with the heart of a patient (different frequency sounds), measuring the heart sounds associated with different categories of patients, such as adults, children, infants, etc.). In addition to the bell attachment 114 described above, the stethoscope chestpiece 20' may also be used with the smaller bell attachment 94 illustrated in FIGS. 6A, 6C, 7A, 8A, 8C, 9A, 10A and the upper diaphragm attachment 102 illustrated in FIGS. 6B, 6E, 7C, 8B, 8D, 9B, 10B. Initially, referring to FIGS. 8A, 9A, and 10A, the smaller bell attachment 94 will be described. Similar to the large bell attachment 114, the small bell attachment 94 comprises an inverted frustoconical body portion 96 with a plurality of internal threads 98 disposed in a bottom cylindrical recess thereof. The plurality of internal threads 98 in the bottom cylindrical recess of the frustoconical body portion 96 threadingly engage with the plurality of external threads 84 disposed on the cylindrical projection or boss extending from the top of the chestpiece body portion 22'. As such, like the large bell attachment 114, a user is able to easily remove the small bell attachment 94 from the chestpiece body portion 22' when it is desired to utilize another type of attachment on the top of the stethoscope chestpiece 20'. Referring to FIGS. 8A and 10A, similar to the transparent non-chill ring or cover 120 of the large bell attachment 114, it can be seen that an upper transparent non-chill ring or cover 100 with upper peripheral recess 101 fits over the inverted frustoconical body portion 96 of the small bell attachment 94. That is, the upper transparent non-chill ring or cover 100 is formed from a resilient material that elastically deforms when the upper peripheral recess 101 of the upper transparent non-chill ring or cover 100 is matingly engaged with the top peripheral rim of the inverted frustoconical body portion 96 of the small bell attachment 94.

Next, with reference to FIGS. 8B, 9B, and 10B, the upper diaphragm attachment 102 will be explained. Similar to the lower diaphragm member 24', the upper diaphragm attachment 102 comprises a body portion 104 with a recess formed in the external surface thereof, an annular projection 110 for accommodating a transparent non-chill ring 108, and a disk-like diaphragm membrane 112. Like the bell attachments 94, 114 described above, the body portion 104 of the upper diaphragm attachment 102 comprises a plurality of internal threads 106 disposed in a bottom cylindrical recess thereof. The plurality of internal threads 106 in the bottom cylindrical recess of the diaphragm body portion 104 threadingly engage with the plurality of external threads 84 disposed on the cylindrical projection or boss extending from the top of the chestpiece body portion 22'. As such, like the bell attachments 94, 114, a user is able to easily remove the upper diaphragm attachment 102 from the chestpiece body portion 22' when it is desired to utilize another type of attachment on the top of the stethoscope chestpiece 20'. Referring to FIGS. 8B, 9B, and 10B, similar to the transparent non-chill ring 90 of the lower diaphragm 24', it can be seen that an upper transparent non-chill ring 108 with circumferential internal groove 109 fits over the annular projection 110 of the diaphragm body portion 104. That is, the upper transparent non-chill ring 108 is formed from a resilient material that elastically deforms when the circumferential internal groove 109 of the upper transparent non-chill ring 108 is matingly engaged with the annular projection 110 of the diaphragm body portion 104. Advantageously, the interchangeability of the stethoscope chestpiece attachments 94, 102, 114 is possible by simply screwing and unscrewing each of the attachments 94, 102, 114 on the chestpiece body portion 22'. In the illustrated embodiment, removable attachments 94, 102, 114 are only provided on the top of the stethoscope chestpiece 20', and not on the bottom of the stethoscope chestpiece 20' which has the non-removable diaphragm member 24'.

Now, the transparent non-chill rings 90, 100, 108, 120 of the stethoscope chestpiece 20' that are disposed on the diaphragm 24' and the attachments 94, 102, 114 will be described in detail. In the illustrated embodiment, each of the non-chill rings 90, 100, 108, 120 is formed from a substantially transparent material so that accumulated particulate matter on the non-chill rings 90, 100, 108, 120 is readily visible to a user of the stethoscope. That is, the non-chill rings 90, 100, 108, 120 are generally clear so that users may more easily identify particulate buildup on, and under the rings 90, 100, 108, 120 (i.e., the material forming the non-chill rings 90, 100, 108, 120 is sufficiently clear so as to enable users to see the body portions 24', 96, 104, 116 disposed underneath the rings 90, 100, 108, 120). That way, users are reminded to clean the rings 90, 100, 108, 120 to decrease cross-contamination, and increase hygiene. Also, if the rings 90, 100, 108, 120 become so contaminated that cleaning them thoroughly is not possible, the rings 90, 100, 108, 120 can be replaced with new rings by disengaging them from their associated attachment body portions 24', 96, 104, 116 (i.e., the rings 90, 100, 108, 120 are readily removable from their attachment body portions 24', 96, 104, 116). In an exemplary embodiment, the non-chill rings 90, 100, 108, 120 may be formed from a transparent polymeric or plastic material comprising a polyvinyl chloride resin (PVC-Resin), a plasticizer, and a stabilizer. In the exemplary embodiment, the transparent polymeric or plastic material may have a tensile strength of greater than or equal to approximately 15.0 megapascals (or ≥15.0 MPa), a tensile strain of greater than or equal to approximately 180% (or ≥180%), a durometer hardness of 91-97 A (Shore OO durometer type), and a density in the range of approximately 1.1 grams per cubic centimeters to 1.3 grams per cubic centimeters (or 1.1 g/cm$^3$ to 1.3 g/cm$^3$). In one or more embodiments, the non-chill rings 90, 100, 108, 120 may be provided with an antimicrobial coating to further decrease cross-contamination and germs.

It is readily apparent that the aforedescribed inventive stethoscope chestpiece 20' offers numerous advantages. First, the stethoscope chestpiece 20' is versatile with sound regulation means (i.e., rotatable acoustic valve assembly 36', 78) and a plurality of different attachments 94, 102, 114 for enabling the stethoscope to be easily used for listening to heart sounds having varying frequency characteristics and/or for treating different types of patients, such as adults, children, and infants. Secondly, the stethoscope chestpiece 20' comprises generally clear non-chill rings 90, 100, 108, 120 that readily enable a user of the stethoscope to identify the buildup of particulate matter on the components of chestpiece that are most frequently in contact with patients.

Any of the features or attributes of the above described embodiments and variations can be used in combination with any of the other features and attributes of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:
1. A chestpiece of a stethoscope, comprising:
a chestpiece body portion having a first end and a second end, said chestpiece body portion including an elongate recess disposed therein;
a rotatable acoustic valve assembly rotatably disposed in said elongate recess of said chestpiece body portion, said rotatable acoustic valve assembly being selectively positionable between a first operative position and a second operative position, said rotatable acoustic valve assembly including a rotatable body portion with a circumferential groove formed therein, said rotatable body portion further including a longitudinal acoustic passageway portion extending a length thereof and a transverse acoustic passageway portion extending generally perpendicular to said longitudinal acoustic passageway portion, said longitudinal acoustic passageway portion being fluidly coupled to said transverse acoustic passageway portion, said circumferential groove of said rotatable body portion of said rotatable acoustic valve assembly being disposed between said transverse acoustic passageway portion of said rotatable body portion and an engaging end portion of said rotatable body portion configured to engage an acoustic tube of a binaural assembly, said rotatable acoustic valve assembly being configured to regulate the transmission of sound waves through said chestpiece of said stethoscope; and a pin positioned within said chestpiece body portion, said pin configured to prevent an axial movement of said rotatable acoustic valve assembly within said chestpiece body portion by engaging with said circumferential groove of said rotatable body portion of said rotatable acoustic valve assembly, said pin comprising a linear body with a first end and a second end, said linear body of said pin extending from said first end proximate to said second end of said chestpiece body portion to said second end disposed in said circumferential groove of said rotatable body portion of said rotatable acoustic valve assembly, said pin being stationarily disposed within an aperture of said chestpiece body portion, and said rotatable body portion of said rotatable acoustic valve assembly being configured to rotate relative to said pin.

2. The chestpiece of a stethoscope according to claim 1, further comprising a spring disposed within said chestpiece body portion, said spring configured to further prevent said axial movement of said rotatable acoustic valve assembly inside said chestpiece body portion.

3. The chestpiece of a stethoscope according to claim 1, wherein said rotatable body portion of said rotatable acoustic valve assembly comprises an interior end portion disposed opposite to said engaging end portion, said interior end portion of said rotatable acoustic valve assembly disposed within said chestpiece body portion, said engaging end portion of said rotatable body portion having a plurality of barbs for engaging said acoustic tube of said binaural assembly.

4. The chestpiece of a stethoscope according to claim 1, further comprising two notches disposed in a circular sidewall bounding said circumferential groove of said rotatable body portion of said rotatable acoustic valve assembly, said two notches being spaced approximately 180 degrees apart from one another, and each of said two notches configured to receive said pin therein.

5. The chestpiece of a stethoscope according to claim 4, wherein a first of said two notches defines said first operative position of said rotatable acoustic valve assembly, and a second of said two notches defines said second operative position of said rotatable acoustic valve assembly, said two notches configured to provide a user with tactile feedback as to a proper positioning of said rotatable acoustic valve assembly in either said first operative position or said second operative position.

6. The chestpiece of a stethoscope according to claim 4, further comprising a spring disposed within said chestpiece body portion, said spring configured to further prevent said axial movement of said rotatable acoustic valve assembly inside said chestpiece body portion, and said spring configured to apply an axial force against said rotatable body portion of said rotatable acoustic valve assembly so that said pin snaps into place in one of said two notches.

7. A chestpiece of a stethoscope, comprising:
a chestpiece body portion having a first end and a second end, said chestpiece body portion including an elongate recess disposed therein;
a diaphragm attached to said first end of said chestpiece body portion;
a rotatable acoustic valve assembly rotatably disposed in said elongate recess of said chestpiece body portion, said rotatable acoustic valve assembly being selectively positionable between a first operative position and a second operative position, said rotatable acoustic valve assembly including a rotatable body portion with a circumferential groove formed therein, said rotatable body portion further including a longitudinal acoustic passageway portion extending a length thereof and a transverse acoustic passageway portion extending generally perpendicular to said longitudinal acoustic passageway portion, said longitudinal acoustic passageway portion being fluidly coupled to said transverse acoustic passageway portion, said circumferential groove of said rotatable body portion of said rotatable acoustic valve assembly being disposed between said transverse acoustic passageway portion of said rotatable body portion and an engaging end portion of said rotatable body portion configured to engage an acoustic tube of a binaural assembly, said rotatable acoustic valve assembly being configured to regulate the transmission of sound waves through said chestpiece of said stethoscope;

a pin positioned within said chestpiece body portion, said pin configured to prevent an axial movement of said rotatable acoustic valve assembly within said chestpiece body portion by engaging with said circumferential groove of said rotatable body portion of said rotatable acoustic valve assembly, said pin being stationarily disposed within an aperture of said chestpiece body portion, and said rotatable body portion of said rotatable acoustic valve assembly being configured to rotate relative to said pin; and a spring disposed within said chestpiece body portion, said spring configured to further prevent said axial movement of said rotatable acoustic valve assembly inside said chestpiece body portion, said spring being disposed between said transverse acoustic passageway portion of said rotatable body portion and said engaging end portion of said rotatable body portion.

8. The chestpiece of a stethoscope according to claim 7, wherein said rotatable body portion of said rotatable acoustic valve assembly comprises an interior end portion disposed opposite to said engaging end portion, said interior end portion of said rotatable acoustic valve assembly disposed within said chestpiece body portion, said engaging end portion of said rotatable body portion having a plurality of barbs for engaging said acoustic tube of said binaural assembly.

9. The chestpiece of a stethoscope according to claim 7, wherein said pin comprises a linear body with a first end and a second end, said linear body of said pin extending from said first end proximate to said second end of said chestpiece body portion to said second end disposed in said circumferential groove of said rotatable body portion of said rotatable acoustic valve assembly.

10. The chestpiece of a stethoscope according to claim 7, further comprising two notches disposed in a circular sidewall bounding said circumferential groove of said rotatable body portion of said rotatable acoustic valve assembly, said two notches being spaced approximately 180 degrees apart from one another, and each of said two notches configured to receive said pin therein.

11. The chestpiece of a stethoscope according to claim 10, wherein a first of said two notches defines said first operative position of said rotatable acoustic valve assembly, and a second of said two notches defines said second operative position of said rotatable acoustic valve assembly, said two notches configured to provide a user with tactile feedback as to a proper positioning of said rotatable acoustic valve assembly in either said first operative position or said second operative position.

12. The chestpiece of a stethoscope according to claim 10, wherein said spring is configured to apply an axial force against said rotatable body portion of said rotatable acoustic valve assembly so that said pin snaps into place in one of said two notches.

13. The chestpiece of a stethoscope according to claim 1, further comprising a component attached to said second end of said chestpiece body portion, said component being disposed above said first end of said linear body of said pin.

14. The chestpiece of a stethoscope according to claim 13, wherein said component comprises a removable bell or a timepiece assembly attached to said second end of said chestpiece body portion.

15. The chestpiece of a stethoscope according to claim 14, wherein said aperture in which said pin is stationarily disposed extends completely through a top portion of said chestpiece body portion and terminates in said elongate recess.

16. The chestpiece of a stethoscope according to claim 9, further comprising a component attached to said second end of said chestpiece body portion, said component being disposed above said first end of said linear body of said pin.

17. The chestpiece of a stethoscope according to claim 16, wherein said component comprises a removable bell or a timepiece assembly attached to said second end of said chestpiece body portion.

* * * * *